(12) United States Patent
Masters et al.

(10) Patent No.: US 8,227,261 B2
(45) Date of Patent: *Jul. 24, 2012

(54) METHODS AND APPARATUS FOR ASSAY MEASUREMENTS

(75) Inventors: Brett P. Masters, Watertown, MA (US); Michael F. Miller, Hollis, NH (US); Alexis F. Sauer-Budge, Lincoln, MA (US)

(73) Assignee: BioScale, Inc., Lexington, MA (US)

( * ) Notice: Subject to any disclaimer, the term of this patent is extended or adjusted under 35 U.S.C. 154(b) by 891 days.

This patent is subject to a terminal disclaimer.

(21) Appl. No.: 11/416,999

(22) Filed: May 2, 2006

(65) Prior Publication Data

US 2007/0117214 A1 May 24, 2007

Related U.S. Application Data

(60) Provisional application No. 60/739,731, filed on Nov. 23, 2005.

(51) Int. Cl.
 *G01N 33/553* (2006.01)
(52) U.S. Cl. ........ 436/526; 436/523; 436/525; 436/168; 435/7.1; 435/7.94; 435/287.2; 435/287.3; 422/68.1; 422/81; 73/24.01; 73/580; 73/599; 73/863
(58) Field of Classification Search ............... 422/58, 422/68.1, 82.05
 See application file for complete search history.

(56) References Cited

U.S. PATENT DOCUMENTS

| | | | |
|---|---|---|---|
| 4,896,098 A | 1/1990 | Haritonidis et al. | 324/663 |
| 4,925,788 A | 5/1990 | Liberti | 435/7 |
| 5,129,262 A | 7/1992 | White et al. | 73/599 |
| 5,313,264 A | 5/1994 | Ivarsson et al. | 356/73 |
| 5,436,161 A | 7/1995 | Bergström et al. | 435/291 |
| 5,445,970 A | 8/1995 | Rohr | 436/526 |
| 5,445,971 A | 8/1995 | Rohr | 436/526 |
| 5,458,852 A | 10/1995 | Buechler | 422/58 |
| 5,479,260 A | 12/1995 | Fattinger | 356/361 |
| 5,656,428 A | 8/1997 | McAllister et al. | 435/6 |
| 5,668,303 A | 9/1997 | Giesler et al. | 73/24.06 |
| 5,705,402 A | 1/1998 | Leland et al. | 436/526 |
| 5,753,518 A | 5/1998 | Karlsson | 436/517 |
| 5,763,191 A | 6/1998 | Knoll et al. | 435/7.1 |
| 5,965,456 A | 10/1999 | Malmqvist et al. | 436/514 |

(Continued)

FOREIGN PATENT DOCUMENTS

EP 1752663 2/2007

(Continued)

OTHER PUBLICATIONS

Pyun et al. (Biosensors and Bioelectronics 13 (1998) 839-845).*

(Continued)

*Primary Examiner* — Sally Sakelaris
(74) *Attorney, Agent, or Firm* — Proskauer Rose LLP

(57) ABSTRACT

Methods and apparatuses for performing assays involving binding material elements with a plurality of bonds over a substantial area of a surface of a resonant device establishing a normalized exposure. The methods and apparatuses also involve controlling an external influence applied to the material elements over a first period of time and measuring a signal during a second period of time that is indicative of the change in the amount of material elements bound to the surface relative to the normalized exposure. In some cases, the measured signals are integrated with respect to time to determine the time averaged amount of material elements bound to the surface.

17 Claims, 5 Drawing Sheets

U.S. PATENT DOCUMENTS

| | | | | |
|---|---|---|---|---|
| 5,972,612 | A | 10/1999 | Malmqvist et al. | 435/6 |
| 6,019,944 | A | 2/2000 | Buechler | 422/58 |
| 6,127,183 | A | 10/2000 | Ivarsson et al. | 436/34 |
| 6,133,043 | A | 10/2000 | Talley et al. | 436/172 |
| 6,143,513 | A | 11/2000 | Löfas | 435/24 |
| 6,289,286 | B1 | 9/2001 | Andersson et al. | 702/19 |
| 6,437,563 | B1 | 8/2002 | Simmonds et al. | 324/239 |
| 6,589,727 | B1 | 7/2003 | Klenerman et al. | 435/4 |
| 6,589,798 | B1 | 7/2003 | Löfas | 436/518 |
| 6,627,404 | B1 | 9/2003 | Buechler et al. | 435/7.1 |
| 6,673,694 | B2 | 1/2004 | Borenstein | 438/411 |
| 6,688,158 | B2 | 2/2004 | Cunningham et al. | 73/24.06 |
| 6,720,710 | B1 | 4/2004 | Wenzel et al. | 310/328 |
| 6,764,860 | B2 | 7/2004 | Lee | 436/518 |
| 6,837,097 | B2 | 1/2005 | Cunningham et al. | 73/24.06 |
| 6,851,297 | B2 | 2/2005 | Cunningham et al. | 73/24.06 |
| 6,946,314 | B2 | 9/2005 | Sawyer et al. | 438/50 |
| 7,000,453 | B2 | 2/2006 | Cunningham et al. | 73/24.06 |
| 7,118,922 | B1 | 10/2006 | Bhansali et al. | 436/518 |
| 7,410,811 | B2 | 8/2008 | Lin et al. | 436/526 |
| 7,598,094 | B2 * | 10/2009 | Masters et al. | 436/526 |
| 7,611,908 | B2 * | 11/2009 | Miller et al. | 436/526 |
| 7,615,381 | B2 * | 11/2009 | Masters et al. | 436/526 |
| 7,629,137 | B2 * | 12/2009 | Sauer-Budge et al. | 435/7.32 |
| 2002/0115198 | A1 | 8/2002 | Nerenberg et al. | 435/287.2 |
| 2002/0182717 | A1 | 12/2002 | Karlsson | 435/287.2 |
| 2003/0012693 | A1 * | 1/2003 | Otillar et al. | 422/58 |
| 2003/0154031 | A1 | 8/2003 | Potyrailo et al. | 702/19 |
| 2004/0002167 | A1 | 1/2004 | Andersson et al. | 436/518 |
| 2004/0038195 | A1 | 2/2004 | Nerenberg et al. | 435/4 |
| 2004/0043423 | A1 | 3/2004 | Bellew et al. | 435/7.1 |
| 2004/0166549 | A1 | 8/2004 | Karlsson et al. | 435/7.92 |
| 2005/0014179 | A1 * | 1/2005 | Karlsson et al. | 435/6 |
| 2005/0019933 | A1 | 1/2005 | Andersson et al. | 436/52 |

FOREIGN PATENT DOCUMENTS

| | | |
|---|---|---|
| WO | WO 91/05261 | 4/1991 |
| WO | WO 01/77624 A2 | 10/2001 |
| WO | WO 2005/111426 | 11/2005 |
| WO | WO 2006/119308 A2 | 11/2006 |

OTHER PUBLICATIONS

Pepper J. et al., "Detection of Proteins and Intact Microorganisms Using Microfabricated Flexural Plate Silicon Resonator Arrays," Sensors and Actuators B, vol. 96, 2003, pp. 565-575.

Choi J-W et al., "A New Magnetic Bead-Based, Filterless Bio-Separator with Planar Electromagnet Surfaces for Integrated Bio-Detection Systems," Sensors and Actuators B, vol. 68, 2000, pp. 34-39.

Dubé et al., "A Si-Based FPW Sensor Array System with Polymer Microfluidics Integrated on a PCB", 2002 IEEE, pp. 460-465.

Grate, et al., "Acoustic Wave Sensors," Sensors Update, 1996, pp. 37-83.

Li, Jishan et al., "Piezoelectric Immunosensor Based on Magnetic Nanoparticles with Simple Immobilization Procedures", Elsevier Science, Analytica Chimica Acta, vol. 481, (2003), pp. 191-198.

S.W. Wenzel, "Applications of Ultrasonic Lamb Waves," dissertation submitted in partial satisfaction of the requirements for the degree of Doctor of Philosophy in Engineering/Electrical Engineering and Computer Sciences, University of California at Davis (1992).

J.W. Grate et al., "Flexural Plate Wave Devices for Chemical Analysis," Analytical Chemistry, vol. 63, 1991, pp. 1552-1561.

J.W. Grate et al., "Frequency-Independent and Frequency-Dependent Polymer Transitions Observed on Flexural Plate Wave Ultrasonic Sensors," Analytical Chemistry, vol. 64, 1992, pp. 413-423.

J.W. Grate et al., "Acoustic Wave Microsensors—Part II" Analytical Chemistry, vol. 65, No. 22, Nov. 15, 1993, pp. 987A-996A.

J.W. Grate et al., "Smart Sensor System for Trace Organophosphorus and Organosulfur Vapor Detection Employing a Temperature-Controlled Array of Surface Acoustic Wave Sensors, Automated Sample Preconcentration, and Pattern Recognition," Analytical Chemistry, vol. 65, No. 14, Jul. 15, 1993, pp. 1868-1881.

D.S. Ballantine, Jr. et al., "Acoustic Wave Sensor—*Theory, Design, and Physico-Chemical Applications*," Academic Press, New York, 1997.

J.C. Pyun et al., "Development of a biosensor for *E. coli* based on a flexural plate wave (FPW) transducer," Biosensors & Bioelectronics, vol. 13, 1998, pp. 839-845.

J. Fritz et al., "Force-mediated kinetics of single P-selectin/ligand complexes observed by atomic force microscopy," Proc. Natl. Acad. Sci. USA vol. 95, Oct. 1998, pp. 12283-12288.

A.W. Wang et al., "A Silicon-based Ultrasonic Immunoassay for Detection of Breast Cancer Antigens," Sensors and Actuators, vol. 49 (1998), pp. 13-21.

T.E. Fisher et al., "The study of protein mechanics with the atomic force microscope," TIBS, vol. 24, Oct. 1999, pp. 379-384.

F. Oesterhelt et al., "Single molecule force spectroscopy by AFM indicates helical structure of poly(ethylene-glycol) in water," New Journal of Physics, vol. 1, 1999, pp. 6.1-6.11.

T. Sulchek et al., "High-speed atomic force microscopy in liquid," Review of Scientific Instruments, vol. 71 (May 2000), pp. 2097-2099.

T. Moir et al., "A Kepstrum approach to Filtering, Smoothing and Prediction," Res. Lett. Inf. Math. Sci., vol. 3, (2002), pp. 135-147, Auckland, New Zealand.

M. Cooper, "Biosensing using rupture event scanning (REVS)™," Measurement Science and Technology, vol. 14, 2003, pp. 1888-1893.

G. Kim et al., "Impedance characterization of a piezoelectric immunosensor Part I: Antibody coating and buffer solution," Biosensors and Bioelectronics, vol. 18, 2003, pp. 83-89.

G. Kim et al., "Impedance characterization of a piezoelectric immunosensor Part II: *Salmonella typhimurium* detection using magnetic enhancement," Biosensors and Bioelectronics, vol. 18, 2003, pp. 91-99.

D. Kim et al., "High-Throughput Cell Manipulation Using Ultrasound Fields," Proceedings of the 26th Annual International Conference of the IEEE EMBS, San Francisco, CA, Sep. 1-5, 2004, pp. 2571-2574.

R. Ekins, "Ambient Analyte Assay," Ch. 3, The Immunoassay Handbook, Ed. D. Wild, Elsevier, Boston, 2005, pp. 46-60.

J.A. Harley et al., "Design of Resonant Beam Transducers: An Axial Force Probe for Atomic Force Microscopy," Proc. ASME Int. Mech. Eng. Congress and Expo, vol. 66, 1998, pp. 247-252.

U. Seifert, "Rupture of Multiple Parallel Molecular Bonds under Dynamic Loading," The American Physical Society, Physical Review Letters, vol. 84, No. 12, Mar. 20, 2000, pp. 2750-2753.

Dultsev et al., ""Hearing" Bond Breakage. Measurement of Bond Rupture Forces Using a Quartz Crystal Microbalance," American Chemical Society, Langmuir, vol. 16, No. 11, 2000, pp. 5036-5040.

G. Bell, "Models for the Specific Adhesion of Cells to Cells," Science, vol. 200, May 12, 1978, pp. 618-627.

E. Evans, "Probing the Relation Between Force-Lifetime-and Chemistry in Single Molecular Bonds," Annu. Rev. Biophys. Biomol. Struct. 2001, 30:105-28, pp. 105-128.

Cozens-Roberts et al., "Receptor-Mediated Adhesion Phenomena," Biophysics Journal, vol. 58, Jul. 1990, pp. 107-125.

J.W. Grate et al., "Acoustic Wave Microsensors—Part I" Analytical Chemistry, vol. 65, No. 21, Nov. 1, 1993, pp. 940A-948A.

* cited by examiner

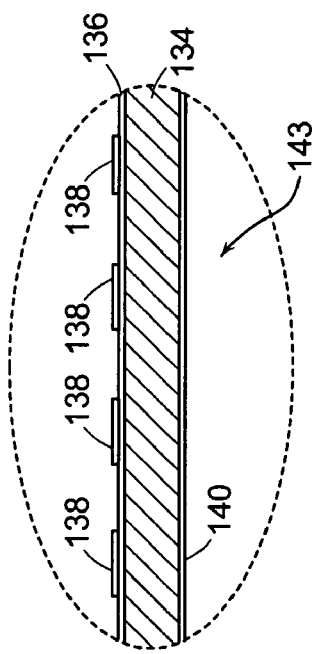
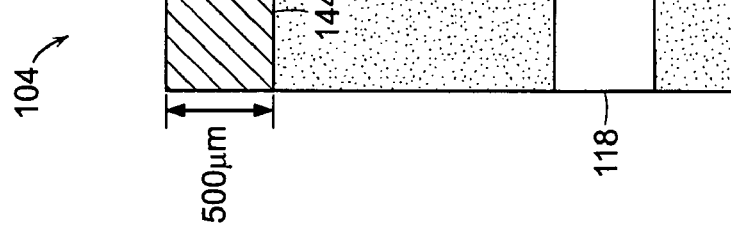

METHODS AND APPARATUS FOR ASSAY MEASUREMENTS

RELATED APPLICATIONS

This application claims priority to U.S. provisional application Ser. No. 60/739,731 filed on Nov. 23, 2005, and entitled "Methods and Apparatus for Assay Measurements," the entirety of which is hereby incorporated herein by reference.

FIELD OF THE INVENTION

The present invention relates to methods and apparatus for performing assay measurements, and in particular, biological assay measurements.

BACKGROUND OF THE INVENTION

Assay measurement techniques seek to measure the amount of a target analyte bound to a capture agent. In some cases, the capture agent is immobilized on a surface, for example, a sensor surface. A second capture agent can be used to simultaneously bind (either by specific, non-specific or cross-reactive association) with the analyte, as in a sandwich assay. When no analyte is present in a sample, small amounts of binding of materials in the sample still can result from non-specific surface association. Typically, the amount of bound target analyte is quantified by comparing the magnitude of a signal recorded after both binding and washing steps (e.g., washing away of non-target material) have been performed with a baseline signal recorded prior to exposing the surface to the sample containing the analyte.

The quantitative methods used in conventional assay measurement techniques are limited in accuracy because they do not account for, for example, variation in the output of different apparatus, provide an effective means for providing multiple measurements over the time period that the assay is conducted or provide a reliable means for removing interfering background materials from the apparatus during operation. Further, some assay measurement techniques require elaborate techniques that employ additional hardware to account for variation in the output of different apparatus.

A need therefore exists for improved assay measurement apparatus and methods.

SUMMARY OF THE INVENTION

The invention, in one aspect, relates to a method for performing an assay. The method involves binding material elements with a plurality of bonds over a substantial area of a surface of a resonant device establishing a normalized exposure. The method also involves changing an external influence applied to the material elements over a first period of time. The method also involves integrating a signal with respect to time during a second period of time to determine the time-averaged amount of material elements bound to the surface.

The invention, in another aspect, features a method for performing an assay that does not require calibration of the assay measurement apparatus prior to running the assay.

The invention, in another aspect, relates to a method for performing an assay. The method involves binding material elements (e.g., magnetic particles, paramagnetic particles, gold particles, microspheres or beads) with a plurality of bonds over a substantial area of a surface of a resonant device establishing a normalized exposure. The method also involves controlling an external influence applied to the material elements over a first period of time. The method also involves measuring a signal during a second period of time that is indicative of the change in the amount of material elements bound to the surface relative to the normalized exposure.

In some embodiments, the method also involves determining the concentration of substances located between the material elements and the surface based on the change in the amount of the material elements bound to the surface during the second period of time relative to the normalized exposure. The substances located between the material elements and the surface can bind the material elements to the surface. In some embodiments, the method also involves correlating the external influence with the amount of material elements that are released (de-bond) from the surface in response to the external influence. In some embodiments, the method also involves integrating values of the measured signal with respect to time to determine the time-averaged amount of material elements bound to the surface.

Controlling the external influence can involve changing the external influence. In some embodiments, the method also involves correlating the change in the amount of material elements bound to the surface with the change in the external influence. Applying an external influence can involve, for example, flowing a fluid over the material elements, through the material elements or across the material elements. Applying an external influence can also involve producing relative acceleration between the material elements and the surface.

In some embodiments, the material elements are magnetic and applying an external influence comprises applying an opposing magnetic gradient to the material elements. In some embodiments, applying an external influence involves exposing the material elements to a constant or time-varying electric field to induce an electrophoretic or dielectrophoretic force that acts on the material elements. In some embodiments, applying an external influence involves exposing the material elements to an acoustic field or fluid flow field generated by the resonant device.

In some embodiments, applying an external influence comprises altering binding force strength between the material elements and the surface. Altering binding force strength can involve altering pH of a fluid, flowing a denaturant over the material elements, altering temperature of a fluid, or combinations thereof. In some embodiments, applying an external influence to the material elements involves increasing amplitude of the relative displacement between the material elements and the surface. In some embodiments, applying the external influence to the material elements involves varying the external influence over the second period of time. In some embodiments, applying an external influence involves generating a force on the material elements that competes with the binding between the material elements and the surface.

In some embodiments, measuring a signal during a second period of time is performed using an apparatus selected from the group consisting of a surface plasmon resonance apparatus, resonant device, acoustic device, flexural plate wave device, quartz microbalance device, and microscope. The surface can be a surface of the apparatus.

Measuring the signal during the second period of time can involve continuously measuring the change in the amount of material elements bound to the surface during the second period of time. In some embodiments, measuring the change in the amount of material elements bound to the surface involves measuring the rate at which the material elements bind to the surface during the first period of time. The first period of time can overlap partially or completely with the second period of time. The bonds can be specific associations, non-specific associations, cross-reactive associations, ionic bonds, covalent bonds, van der Waals bonds, hydrogen bonds or polar bonds.

In some embodiments, the material elements are exposed to the substances within a sample prior to binding the material elements to the surface of the resonant device. In some embodiments, the method also involves determining the concentration of the substances located in the sample based on the concentration of the substances located between the material elements and the surface.

The invention, in another aspect, features an apparatus for performing an assay. The apparatus includes a resonant device that has a surface. The apparatus also includes a binding substance or means for binding that is capable of binding a plurality of material elements (e.g., magnetic particles, paramagnetic particles, gold particles, microspheres or beads) to the surface and of sandwiching a substance between the plurality of material elements and the surface to form a plurality of bonds between the substance and the plurality of material elements and to establish a normalized exposure. The apparatus also includes a source for applying an external influence to the material elements over a first period of time. The apparatus also includes a measurement device for measuring a signal that is indicative of the change in the amount of material elements bound to the surface relative to the normalized exposure.

In some embodiments, the source for applying an external influence controls flow of a fluid over the material elements, through the material elements or across the material elements. In some embodiments, the material elements are magnetic and the source for applying an external influence applies an opposing magnetic gradient to the material elements. In some embodiments, the source for applying an external influence exposes the material elements to a constant or time-varying electric field to induce an electrophoretic or dielectrophoretic force that acts on the material elements. In some embodiments, the source for applying an external influence exposes the material elements to an acoustic field or fluid flow field generated by the resonant device.

The resonant device can be, for example, an acoustic device, flexural plate wave device, surface acoustic wave device, lamb wave device, resonant cantilever device, shear harmonic surface acoustic wave device, acoustic plate mode device or quartz crystal microbalance device. In some embodiments, the measurement device is a surface plasmon resonance apparatus, resonant device, acoustic device, flexural plate wave device, quartz microbalance device, or microscope. In some embodiments the source for applying an external influence is also the measurement device.

The invention, in another aspect, relates to a method for performing an assay. The method involves binding material elements with a plurality of bonds over a substantial area of a surface establishing a normalized exposure. The method also involves applying an external influence to the material elements over a first period of time. The method also involves measuring an optical signal during a second period of time that is indicative of the change in the amount of material elements bound to the surface relative to the normalized exposure. The method also involves integrating values of the optical signal with respect to time to determine the time-averaged amount of material elements bound to the surface.

In some embodiments, the method also involves determining the concentration of substances located between the material elements and the surface based on the change in the amount of the material elements bound to the surface during the second period of time relative to the normalized exposure.

In some embodiments, the substances located between the material elements and the surface bind the material elements to the surface.

In some embodiments, the method also involves correlating the external influence with the amount of material elements that are released from the surface in response to the external influence. Applying an external influence can involve flowing a fluid over, through or across the material elements. In some embodiments, applying an external influence involves exposing the material elements to a constant or time-varying electric field to induce an electrophoretic or dielectrophoretic force that acts on the material elements. In some embodiments, applying an external influence involves exposing the material elements to an acoustic field or fluid flow field generated by the resonant device.

In some embodiments, applying an external influence involves altering binding force strength between the material elements and the surface. Altering binding force strength can involve altering pH of a fluid, flowing a denaturant over the material elements, altering temperature of a fluid, or combinations thereof.

In some embodiments, measuring an optical signal during a second period of time is performed using an apparatus selected from the group consisting of a surface plasmon resonance apparatus, microscope, or fluorescence measurement apparatus. The surface can be a surface of the apparatus.

The particles can be, for example, magnetic particles, paramagnetic particles, gold particles, microspheres or beads. In some embodiments, the particles are fluorescent. In some embodiments, measuring an optical signal involves measuring reflectivity, transmission or fluorescence of the particles or a substance bound to the particles.

The invention, in another aspect, features an apparatus for performing an assay. The apparatus includes a surface, wherein a binding substance or means for binding is capable of binding a plurality of materials to the surface and of sandwiching a substance between the plurality of materials and the surface to form a plurality of bonds between the substance and the plurality of materials and to establish a normalized exposure. The apparatus also includes a source for applying an external influence to the material elements over a first period of time. The apparatus also includes an optical measurement device for measuring a signal that is indicative of the change in the amount of material elements bound to the surface relative to the normalized exposure, wherein integrating values of the optical signal with respect to time determines the time-averaged amount of material elements bound to the surface.

In some embodiments, the source for applying an external influence controls flow of a fluid over, through or across the material elements. In some embodiments, the material elements are magnetic and the source for applying an external influence applies an opposing magnetic gradient to the material elements. The optical measurement device can be, for example, an apparatus selected from the group consisting of a surface plasmon resonance apparatus, microscope or fluorescence measurement apparatus.

In some embodiments, the source for applying an external influence exposes the material elements to a constant or time-varying electric field to induce an electrophoretic or dielectrophoretic force that acts on the material elements. In some embodiments, the source for applying an external influence exposes the material elements to an acoustic field or fluid flow field generated by a resonant device. The particles can be, for example, magnetic particles, paramagnetic particles, gold particles, microspheres or beads.

The invention, in another aspect, features an apparatus for performing an assay. The apparatus includes means for binding material elements with a plurality of bonds over a substantial area of a surface of a resonant device establishing a normalized exposure. The apparatus also includes means for controlling an external influence applied to the material elements over a first period of time. The apparatus also includes means for measuring a signal during a second period of time that is indicative of the change in the amount of material elements bound to the surface relative to the normalized exposure.

BRIEF DESCRIPTION OF THE DRAWINGS

The foregoing and other objects, feature and advantages of the invention, as well as the invention itself, will be more fully understood from the following illustrative description, when read together with the accompanying drawings which are not necessarily to scale.

FIG. 2 is an expanded view of a portion of the assay measurement apparatuses shown in FIG. 1A and FIG. 1B.

DETAILED DESCRIPTION OF ILLUSTRATIVE EMBODIMENTS

Figure 1A:
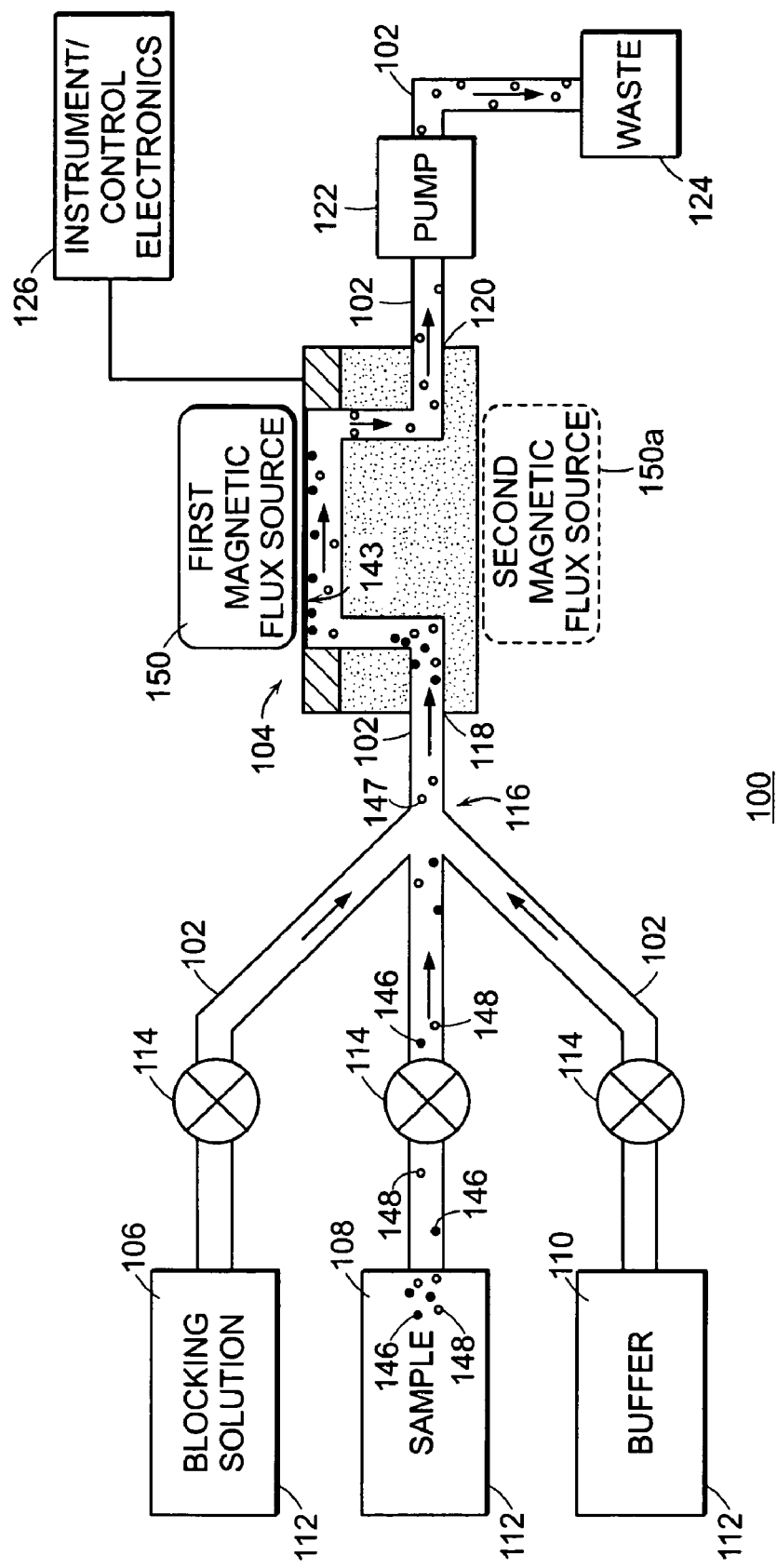
FIG. 1A is a schematic illustration of an assay measurement apparatus used in conducting assay measurements.

The present invention is drawn to assay measurement methods that involve comparing binding (or association) and de-binding (or dissociation) strength between the surface of a plurality of material elements and a second surface in the presence of an external influence that acts on one, or both sets, of the surfaces. The external influence competes with the binding between the material elements and the second surface. Particular embodiments of the present invention also involve, for example, measuring a signal that is indicative of the change in the amount of material elements bound to the second surface relative to a normalized exposure. Another embodiment of the invention also involves integrating the measured signal with respect to time to determine the time-averaged amount of material elements bound to the second surface.

Embodiments of the present invention do not require an absolute calibration of the assay measurement apparatus. For example, in some embodiments the surface to which the plurality of material elements are bound is the surface of a resonant device. The resonant device measures the relative frequency shift of the device and does not require an absolute frequency or amplitude calibration of the assay measurement apparatus electronics. Additionally, because the method involves measuring a relative change in the amount of material accumulated on a single device by comparing the signal at multiple time points, the response of the device itself (e.g., an FPW device) to material accumulating on its surface does not have to be calibrated prior to running an assay other than, for example, calibration for variations in the biological reagents. Calibration for variations on the biological reagents is sometimes done on a lot by lot basis and involves the use of controls. Aside from this calibration, embodiments of the invention have the advantage of being able to reduce the amount of calibration required of the assay measurement apparatus (the means of signal transduction). This enables lower cost manufacture of the devices because there is no required calibration step during assembly and test.

Additionally, methods of the invention provide for an assay that is robust to variations in the amount of material elements (e.g., beads) interacted with or mixed with (by, for example, pipette) a sample to bind with or capture a particular analyte. Because the methods normalize for the total amount of material elements collected on the surface of the device during the accumulation period, the method is generally not sensitive to these variations.

The reduced calibration requirements of an assay measurement apparatus that includes a resonant device is especially advantageous for a decentralized measurement system. To be approved for operation of an assay outside of a laboratory environment, the system must operate without daily calibration. The ability to operate without direct calibration and the improved immunity to variations in the added reagent (e.g., beads) provides an improved assay measurement method.

Various measurement assay formats and apparatus are contemplated that are within the scope of the present invention. For example, one or both of the surfaces can have capture agents on the surfaces. A sandwich assay can, for example, be performed in which the surface of a plurality of material elements (e.g., beads) is coated with a capture agent that is capable of binding with a particular substance (e.g., particular analyte). The capture agent coated material elements are exposed to a sample containing the particular analyte. A second surface (e.g., a surface of a resonant device or an optical surface) is coated with a capture agent that also is capable of binding with the particular analyte. The capture agent coated material elements are exposed to the second surface. The appropriate assay measurement apparatus (e.g., a resonant device-based measurement apparatus or surface plasmon resonance apparatus) is then employed to, for example, detect the presence of the particular analyte bound to the second surface.

A competitive assay is an example of another assay format that also can be performed which also can benefit from the application of methods of the present invention. The surface of a plurality of material elements (e.g., beads) is coated with a capture agent that is capable of binding with a particular substance (e.g., a particular analyte). The capture agent coated material elements are exposed to a sample containing the particular analyte. A second surface (e.g., a surface of a resonant device or an optical surface) is coated with a capture agent that is capable of binding with the material elements. The capture agent coated material elements are exposed to the second surface. The capture agent coated material elements that do not become populated with the particular analyte are prone to bond with the second surface. The capture agent coated material elements that do become populated with the particular analyte are less likely to bond with the second surface. In this manner, capture agent coated material elements will bond with low net strength to the second surface if the sample contains a large amount of the particular analyte.

In one embodiment of the invention, a substance (e.g., an analyte) in a fluid sample binds to a surface of a material element (e.g., a magnetic bead) to form a substance-material element complex. The complex is transported and localized onto a device surface (e.g., a surface of a resonant device) by applying a gradient magnetic field to the system. The magnetic field induces a polarization in the magnetic material of the material element that is aligned with the local magnetic field lines. The material element experiences a net force in the direction of the gradient, causing the material element to migrate toward regions of higher field strength. The magnetic field distribution is tailored to draw complexes within the fluid sample towards the device surface and to distribute them across the device surface. The extraneous, background components in the fluid sample (e.g., cells, proteins—components that are not target components) generally have a much lower magnetic susceptibility as compared to the magnetic material elements, and so the magnetic field does not significantly influence them. Hence, only a very small fraction of the background component material interacts with the device surface.

FIG. 1A is a schematic illustration of one embodiment of an assay measurement apparatus 100 for use in conducting assay measurements, according to the present invention. The system 100 includes a network of channels 102 for transporting various test solutions (also referred to herein as "test fluids" or "fluids") to a surface 143 of an assay device 104. The following U.S. Patents and Patent Applications, all of which are hereby incorporated by reference, describe examples of the various types of assay devices suitable for use in the present assay measurement apparatus 100: U.S. Pat. No. 5,129,262, U.S. Pat. No. 5,189,914, U.S. Pat. No. 6,688,158 B2, U.S. Pat. No. 6,851,297, U.S. Pat. No. 5,668,303, U.S. Pat. No. 5,836,203, and U.S. Patent Application Publication No. 2004-0038195.

For example, U.S. Pat. No. 5,129,262 describes an ultrasonic sensor that has a thin planar sheet of material forming a Lamb wave propagation medium. Lamb waves, also known as plate-mode waves, can propagate only through a material of finite thickness. In contrast to surface acoustic waves (SAWs), which require a propagation medium having a thickness on the order of hundreds of times the wavelength of the propagating SAW, Lamb waves require a propagation medium which is at most only several wavelengths thick, and typically only a fraction of the wavelength of the propagating Lamb wave. The thickness of the sheet is no greater than about twenty microns. A Lamb wave generator generates Lamb waves in the planar sheet, and an output device produces an electrical signal that represents the propagation characteristics of the Lamb waves propagating along the sheet. A measuring device measures selected characteristics of the output electrical signal. The planar sheet has some physical characteristics that depend upon the value of a measurand acting on the sheet, and those physical characteristics consequently determine the propagation characteristics of the Lamb waves that propagate along the sheet. Since the electrical signal from the output device represents the propagation characteristics, the electrical signal also represents the value of the measurand acting on the sheet.

The Lamb wave device described in U.S. Pat. No. 5,129,262 can be employed, for example, in biological sensing. The planar sheet described above can be pre-coated with a capture agent, so that the frequency of the device changes upon immersion in or contact with a liquid that contains an analyte capable of binding with the capture agent. Capture agent attachment to the analyte at the surface of the propagation medium acts to alter the wave velocity of the Lamb waves in the sheet. The change in wave velocity causes the oscillation frequency to change in a delay line oscillator form of the device. Also, the sheet may be made of a porous and permeable material, allowing the coating of capture agent over a greater surface area of the sheet and also allowing the analyte containing liquid to be flowed through the membrane, in order to speed up the capture agent-analyte attachment. Other biological interactions may also be sensed, and additional applications include immunoassay, clinical laboratory testing, in vivo biomedical monitoring, and biomedical research.

The test solutions used in the described embodiment, for example a blocking solution 106, a sample 108, and a buffer 110, are sourced from reservoir containers 112. The channel path from each of the reservoirs 112 is gated with a valve 114 to control the flow of a particular test solution to a combination point 116 leading to an entry port 118 of the assay device 104. The test solution flows through the assay device 104 and exits via an exit port 120, which leads to a pump 122. The pump 122 draws the test solution through the network of channels 102 and through the assay device 104, and directs the test solution to a waste receptacle 124.

Figure 1B:
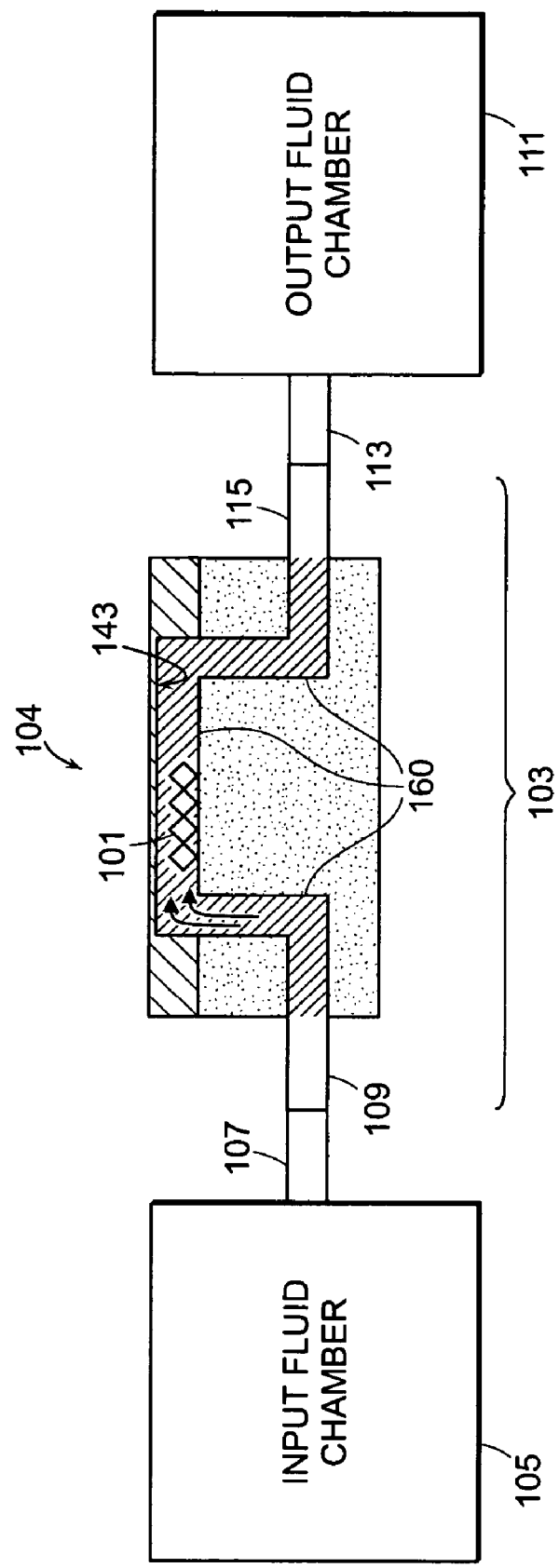
FIG. 1B is a schematic illustration of another embodiment of an assay measurement apparatus.

FIG. 1B shows another embodiment of the assay measurement apparatus 100. This embodiment packages the assay device 104 and its associated fluid chamber 160 as a cartridge 103 (i.e., a consumable component that can be removed and replaced). Some embodiments may include a fluid control device 101 such as a plug, obstruction or baffle that alters the flow through the device 104. In one embodiment, the fluid control device 101 operates to cause the fluid flow through the device 104 to pass closer to the surface 143 than if the fluid control device 101 was not present. Further, the source of input test solutions is shown as an input fluid chamber 105 that has an outlet 107 for directing the test solutions into the inlet 109 of the cartridge 103. In some embodiments, magnetic particles are initially located in the input fluid chamber 105 and the fluid containing the analyte is mixed with the magnetic particles in the input fluid chamber 105 and then directed into the cartridge 103 in which the device 104 is located. The magnetic particles may be combined within the input fluid chamber 105 with the fluid containing the analyte by a device (e.g., by the action of a pump or a magnetic agitator).

FIG. 1B further shows an output fluid chamber 111 with an inlet 113 that receives fluid from the outlet 115 of the cartridge 103. This output fluid chamber 111 may include one or more of the fluid control devices described herein, and it may include one or more mechanisms for storing and/or treating waste fluid. In some embodiments, the apparatus 100 does not include a chamber 160. In some embodiments, fluids are provided to the surface 143 of the device 104 by a single, linear fluid channel or flow path adequate to support the flow of the fluids to the surface 143 of the device 104.

In at least one embodiment, the junction where the outlet 107 of the input fluid chamber 105 meets the inlet 109 of the cartridge 103 is constructed and arranged to allow repeatable connection and disconnection. Similarly, the junction where the outlet 115 of the cartridge 103 meets the inlet 113 of the output fluid chamber 111 is constructed and arranged to allow repeatable connection and disconnection. In some embodiments, these junctions are constructed and arranged to require tools for connection and disconnection, such as threaded couplings that require a wrench or other such tool to affect the coupling and decoupling. In other embodiments, these junctions are constructed and arranged to allow quick and easy manual connection and disconnection, without any extra tools or accessories. Such couplings, both requiring and not requiring tools, are known in the art. In some embodiments, there are multiple input fluid chambers and output fluid chambers. In some embodiments, one or more input and/or output fluid chambers are part of the cartridge 103. Further, in some embodiments, one or more sources of magnetic flux are part of the cartridge 103.

The device 104 of FIGS. 1A and 1B is shown in more detail in FIG. 2A. In this embodiment, the assay device 104 is an FPW device. Strain energy is carried in bending and tension in the FPW device 104. In some embodiments, it is desirable for the thickness-to-wavelength ratio of the FPW device 104 to be less than one, and in some cases much less than one. In general, the wavelength "λ" of the FPW device 104 is approximately equal to the pitch of the interdigitated electrodes as described herein. In one embodiment, the thickness-to-wavelength ratio of the FPW device 104 is 2 μm/38 μm. In other embodiments, the FPW device 104 is designed to isolate a particular mode (e.g., any mode from the zero$^{th}$ order mode to higher order modes) or bandwidth of modes associated with the device. For example, an FPW device 104 having a thickness/wavelength of 2 μm/38 μm as described above would isolate the 80$^{th}$ mode of the FPW device 104. The FPW device 104 can be designed to achieve this effect by selecting a particular pattern for the interdigitated electrodes deposited on the device. In one embodiment, the FPW device 104 is rectangular in shape. The FPW device 104 can, alternatively, be circular or elliptical, or some other planar shape.

In general, the FPW device 104 is constructed from a silicon wafer 130, using micro-fabrication techniques known in the art. In the described embodiment, a cavity 132 is etched into the wafer 130 to produce a thin, suspended membrane 134 that is approximately 1.6 mm long, 0.4 mm wide and 2 μm thick. The overall wafer 130 thickness is approximately 500 μm, so the depth of the cavity 132 is just slightly less than the wafer 130 thickness. A 0.5 μm layer 136 of aluminum nitride (AlN) is deposited on the outer surface (i.e., the surface opposite the cavity 132) of the membrane 134, as shown in the expanded view insert of FIG. 2A. Two sets of interdigitated metal electrodes 138 are deposited upon the AlN layer. A thin layer 140 of gold (approximately 500 angstroms) is deposited on the inner surface (i.e., the surface facing the cavity 132) of the membrane 134 to facilitate immobilization of capture agents (described in more detail herein).

In some embodiments, micromachined devices (using, for example, MEMS processes) are preferred because they can be manufactured to have substantially planar sense areas (e.g., surface 143) that can be easily and reliably wetted. In some embodiments, coatings or surface treatments are applied to the device surfaces to improve the wettability of the surfaces. Referring to FIGS. 2 and 2A, the fluid channel geometry near the surface 143 is accurately defined by the micromachining processes of etching the cavity using, for example a DRIE etching process or a controlled KOH etching process. Accurate fluid volume flow rates are provided to the surface 143 of the apparatus 100 as an external influence. The combination of controlled fluid flow and the defined fluid channel results in precise flow speeds over the sensor surface. The precise flow control allow for discrimination between small differences in the association strengths of the different particles that adhere to the surfaces of the devices.

FPW devices (e.g., the device 104 of FIG. 2) are advantageous for performing assay measurements because the devices are thin, thereby allowing for close engagement of a magnetic field at or near the surface of the device which generates high magnetic gradients within the exposed fluid. High magnetic gradients provide a strong attractive force for material elements (e.g., paramagnetic particles) that allows for more efficient extraction of lower concentrations of these particles from the exposed samples. High magnetic gradients also allow for the assay to be conducted with stronger flow conditions while attracting these material elements to the transducer surface which reduces nonspecific adherence (e.g., adherence of cells) to the surfaces of the device. The ability to use lower concentrations of particles allows for lower detection limits because more analyte per unit area of particle is captured which gives rise to a stronger measurable association/dissociation effect with the sensor surface.

In operation, instrument/control electronics 126 (referring to FIG. 1A) apply a time-varying electrical signal to at least one set of electrodes 138 to generate vibrations in the suspended membrane 134. The instrument/control electronics 126 also monitor the vibrational characteristics of the membrane 134 by receiving a sensor signal from at least a second set of electrodes 138. When liquid is in contact with the cavity side 132 of the membrane 134, the maximal response of the plate structure is around 15-25 MHz. The instrument/control electronics 126 compare a reference signal to the sensor signal from the second set of electrodes to determine the changes in the relative magnitude and phase angle of the sensor signal as a function of frequency. The instrument/control electronics 126 interpret these changes to detect the presence of the particular targeted analyte. In some embodiments, the instrument/control electronics also determines, for example, the concentration of the analyte on the inner surface 143 of the membrane 134.

In some embodiments, a resonant sensor system is advantageous because it provides real time signals that represent a spatial integration, weighted with respect to the mode shape of the resonant device, of interaction with material matter near the sensor surface. This type of signal may be advantageous over an optical frame by frame image sequence because each frame would have to be post processed to assess the amount of material matter within the frame. Real time signals allow for modest to high fidelity temporal observation and integration of the relative rate at which material elements or analyte bind on to (associate with) the surface of the resonant device and the rate at which material elements or analyte is released (dissociate from) from the surface of the resonant device. In this way, the statistical nature with which material associations are made with the surface and dissociations from the surface under controlled external influences are observed and accumulated over time to gain a normalized time aggregate signal.

Capture agents targeting the analyte of interest are immobilized on the thin layer of gold 140 covering the inner surface of the membrane 134, as described herein. In one embodiment, thiol-terminated alkyl chains are linked to the gold surface forming a self-assembled monolayer (SAM). A fraction of the SAM chains are terminated with reactive groups (e.g., carboxyl) to allow covalent linking of capture agents to the SAM chains using biochemical process steps known in the art. The remainder of the SAM chains are terminated with non-reactive groups, preferably ones that have a hydrophilic character to resist nonspecific binding (e.g., oligomers of ethylene glycol). Other surface chemistries are described in the literature and can be used to produce a capture surface.

The FPW device 104 is packaged to allow electrical connections to the electrodes 138 on the outer surface of the membrane 134. Additionally, the FPW device 104 is mechanically supported by a channel block 142, to allow for the inner surface of the membrane 134 to contact the test solutions and an interface is provided for contacting the sensor surface 143 with the liquid sample. The channel block 142 creates a path (e.g., the fluid chamber 160 in FIG. 1B) for the test solutions to flow from an input port 118, past the inner surface of the membrane 134 and then out of an exit port 120. A seal 144 is formed between the FPW device 104 and the channel block 142 to prevent test solutions from escaping from the channels 102 formed within the combination of the FPW device 104 and the channel block 142. The channel block 142 thus forms a fluid chamber, of which the FPW device 104 comprises one of the interior walls.

The channels 102 through the combination of the FPW device 104 and the channel block 142 are approximately 0.5 mm in diameter. The channel block 142 can be formed from a variety of materials, including plastic, metal or ceramic, among other materials.

The apparatus 100 includes one or more fluid control devices for changing at least one fluid property, such as flow, pressure, or trajectory to name a few, within the system 100. The pump 122 and valves 114 shown in FIG. 1A that direct and control the flows of various test solutions through the device and over the surface 143 (as required to execute a test protocol) are all examples of fluid control devices. In general, a fluid control device changes the at least one fluid property in the vicinity of at least one surface within the fluid chamber 160 of the device 104. Generally, this is done to distribute the magnetic particles along at least a portion of the surface 143. As described above, in some embodiments the fluid control device is a pump (e.g., a peristaltic pump, centrifugal pump, rotary pump, electro-osmotic pump). In some embodiments, the pump is located on the entrance side of the fluid chamber, and in other embodiments the pump is located on the exit side of the fluid chamber. In some embodiments, the device is a flow diverter (e.g., a plug, obstruction wall or baffle) that is disposed relative to the fluid chamber to alter the fluid flow in the vicinity of the at least one interior surface of the fluid chamber.

Referring to FIG. 1A, a single pump 122 is positioned on the waste side of the assay device 104. Suction that the pump 122 generates draws buffer 110 or analyte in the sample 108 from their respective reservoir containers 112 on the supply side of the device 104. Valves 114 are positioned on the supply side of the device 104 to control which test solution is directed over the surface 143 at any time during the test protocol. The pump 122 controls the flow rate of the test.

A device for regulating temperature (e.g., a thermoelectric cooler) may be associated with the device 104 and channel block 142. This reduces the impact of variable environmental conditions on the device 104 output by maintaining the device 104 at a relatively constant, known temperature. In an alternative embodiment, a temperature sensor is included within the apparatus 100, for example as part of the device 104. The sensor signal from the device 104 is scaled, at a specific instant in time (or during a period of time), based on the output of the temperature sensor, in order to produce a signal that is independent of the effects of temperature variations. This scaling could be done based on a mathematical model, or an analytical model, or some hybrid combination of a mathematical and analytical model.

In some embodiments of the apparatus 100, a filter is included in the path of the test solution to selectively filter particles (e.g., magnetic particles and biological materials) of a particular size to prevent them from entering the fluid chamber. By way of example, a particular testing protocol may include steps for changing the filter during the test. This would allow different types (i.e., sizes) of analytes and magnetic particles to be directed into the fluid chamber, and thereby tested by the apparatus 100, during different portions of the test.

In one embodiment, the material elements are magnetic particles (e.g., paramagnetic or super-paramagnetic beads or microspheres) that have their surfaces coated with a capture agent, and which are mixed with a sample containing the analyte. After a prescribed mixing time analyte-material element complexes 146 result as do particles 147 that have bound nonspecific materials and particles 148 that have bound nothing. The particles 146, 147 and 148 are located in the sample reservoir 112.

The apparatus 100 further includes a magnetic field inducing structure 150 for producing magnetic flux in the vicinity of the membrane 134. In FIG. 1A, the source of magnetic flux is a retractable magnet 150 arranged to normally be in close proximity to the membrane 134 of the device 104. When the magnet 150 is in close proximity to the membrane 134, the magnet 150 produces a significant gradient magnetic field in the vicinity of the membrane 134. Under control of the instrument/control electronics 126, the retractable magnet 150 can be retracted away from the membrane 134 by a distance sufficient to substantially reduce magnetic fields in the vicinity of the membrane 134. In one embodiment, when in close proximity to the membrane 134, the magnet 150 is situated approximately 200 µm from the surface 143 of the membrane 134. In another embodiment, when in close proximity to the membrane, the magnet 150 is situated between about 50 µm to about 100 µm from the surface 143 of the membrane 134.

When the magnet 150 is in close proximity to the membrane 134, the magnet 150 provides a source of magnetic flux to draw the magnetic particles from the sample to the surface 143. The analyte-particle complexes 146, as well as particles 147 with nonspecifically bound material and particles 148 with nothing bound migrate from the liquid sample until they encounter the surface 143. The analyte binds with the capture agent on the surface 143. Thus, the analyte forms a link between the magnetic particle and surface. The particles 147 with non-specifically bound material and particles 148 with nothing bound are held at the surface 143 by the magnetic field. Additionally, weak binding forces can act between the particles 146, 147, and 148 and the surface 143. During the wash step of the protocol (described in more detail herein), the magnet 150 is retracted to reduce the magnetic force experienced by the particles that have accumulated at the surface 143. The wash flow rate is increased to remove particles 147 and 148 that are not bound to the surface 143 by analyte. Since the particles 147 with nonspecifically bound material as well as particles 148 with nothing bound are more weakly linked to the surface 143 than the analyte-particle complexes 146, they release from the surface 143 at a lower wash flowrate (and corresponding hydrodynamic force). Hence, removing the magnet 150 (i.e., substantially reducing the magnetic force experienced by the particles 146, 147, and 148 at the surface 143) is used to distinguish between particles with analyte 146 from those without (particles 147 and 148). One technique for engaging and retracting the magnet 150 is to mount it on a carriage (not shown) that is actuated by a cam system (not shown).

The magnet 150 material, geometry and distance from the surface 143 determine the field shape and field gradient, and therefore, the force that the analyte-particle complexes 146 experience. High strength permanent magnets for use as the retractable magnet 150 are available commercially. For example, 1 mm diameter cylindrical NdFeB magnets can be purchased from several vendors (e.g., Dexter Magnetic Technologies). In one embodiment, a 1 mm diameter and 5 mm long NdFeB magnet 150 is positioned within 0.1 mm of the surface 143 when engaged. When retracted the magnet 150 is at least 0.5 mm from the surface 143. Since the membrane 134 of the device 104 is very thin (2 µm) and made of nonmagnetic materials (e.g., silicon, aluminum nitride or gold), the membrane 134 does not significantly perturb the magnetic field on the surface 143 side of the device 104. As a result, very high magnitude magnetic fields and large field gradients can be achieved, as is necessary for high collection efficiencies.

The sample flow rate through the channels 102 is determined (e.g., specified by an operator) by the residence time necessary for good collection efficiency. The sample flow rate is adjusted so that the average velocity over the surface 143 is between about 1 and about 5 mm/s. With an iron oxide paramagnetic particle with a diameter of approximately 3 μm, collection efficiencies approaching 50% can be achieved.

Other configurations of the source 150 of magnetic flux (i.e., the magnet) may be used. For example, an electromagnet can be used instead of a permanent magnet. The electromagnet includes pole pieces that extend to focus the field flux near the surface 143 of the device 104.

Alternatively, a magnetizable material can be fashioned and positioned adjacent to the surface 143 (within 0.1 mm), and a separate magnet combined with an open face of the magnetizable material to induce a magnetic field in the magnetizable material. The magnetic field induced in the material serves to locate desirable field gradients near the surfaces 143. In this way, large, low cost magnets can be used, and a single magnet can be used to address multiple sensors, depending on the fashioning of the material. Examples of useful materials for this purpose are pure iron, high mu metals such as alloy 49 (high nickel content iron), silicon steels (1-2% silicon typical). An advantage of using such a magnetizable material with an associated magnet is that the sensor assembly can be simplified, allowing lower cost manufacturing. A low precision actuator can be used for engaging and retracting the magnet since the magnet need only contact the ferromagnetic core or be fully withdrawn. In the described embodiment where the magnet 150 is positioned in close proximity to the surface 143, a higher level of precision is required to achieve good assay repeatability. Although there is some loss of field strength with this approach, it is still possible to design the overall system to achieve good capture efficiencies (e.g., >10%).

The shape of the tip of the field inducing structure (e.g., magnet or ferromagnetic material) may be tailored to enhance and/or concentrate the field gradient at the surface 143 of the device 104. Since the size of the device 104 (e.g., 0.3 mm×1.6 mm) is typically smaller than conventionally formed magnets or machined inductors, the portion of the field inducing structure adjacent to the membrane 134 can be tapered to concentrate the magnetic field in one or more locations on the surface 143. Tapering the tip acts to increase both the local field magnitude and the local field gradients. For example, a wedge-shaped tip is well suited to the device geometry illustrated in FIG. 2.

One embodiment of the apparatus 100 includes an optional second source 150a of magnetic flux that opposes or partially opposes the first source 150 of magnetic flux. This second source 150a of magnetic flux can be used to dislodge some of the magnetic particles that have adhered to the surface 143. It may, for example, dislodge magnetic particles 148 that do not have any bound analyte; they would not be as strongly attached to the surface 143 as the particles 146 that do have bound analyte. In some embodiments, the first source 150 of magnetic flux is turned off or moved away from the surface 143 and then, the second source 150a of magnetic flux is positioned relative to the at least one surface of the fluid chamber to selectively remove magnetic particles. This may be done, for example, to remove magnetic particles 148 that do not have any bound analyte and therefore they are not as strongly bound to the surface 143. This would achieve a similar effect as increasing the flow of fluid to remove magnetic particles 148 that do not have any bound analyte.

Controlling the distribution of the analyte-particle complexes 146 on the surface 143 of the device 104 can improve the device performance, since the device 104 has a suspended membrane 134 and not all parts of the membrane 134 contribute equally to the moving mass of the detectable resonance. For example, the apparatus 100 can be constructed and arranged to distribute the analyte-particle complexes 146 within one third of the device 104 width along the middle two-thirds of the centerline of the long axis of the membrane 134. Taking into account flow field effects, the shape of the tip of the field-inducing structure (e.g., magnet 150) can be such that the field magnitude and field gradient increase in the direction of the flow over the sensor membrane 134. That is, analyte-particle complexes 146 in the downstream regions, where the boundary layer is partially depleted of analyte, experience a higher field and field gradient than do analyte-particle complexes 146 in the upstream regions.

In general, the apparatus 100 can be constructed and arranged to concentrate magnetic particles in one or more particular regions of the surface 143. The response of the device 104 may not be uniform over the surface 143 due to characteristics of the fabrication materials or the specifics of the apparatus design. Thus, high sensitivity regions of the device 104 may be non-uniform and asymmetrical with respect to the long and short axis centerlines of the device 104. Thus, the tip of the field inducing structure may be shaped to concentrate magnetic particles in the region or regions of highest sensitivity.

Varying the flow rate through the device 104 can also be used to achieve a more uniform coverage of analyte-particle complexes 146 for a given magnetic field distribution. For a given field, magnetic particles interact with the surface 143 as determined by the bulk fluid flow rate, much like a ballistic object might fall in the presence of the gravity body force. In this case, however, the magnetic induced force dominates. By varying the flow rate, the analyte-particle complexes 146 can be caused to interact with the surface 143 at substantially different locations along the stream-wise flow direction. Furthermore, as the magnetic particles pile up (a non-desirable occurrence if they are to be exposed to the surface 143) the flow can be reversed and subsequently pulsed forward in order to pull the pile over and thus distribute more particles over the surface 143. In one embodiment of the apparatus 100, selective location of the magnetic particles along the surface 143 is achieved by, for example, selectively altering, over the course of the detection protocol, either one or both of the magnetic flux source 150 and the property or properties of the fluid flow along the surface 143.

One embodiment of the apparatus 100 includes a device (e.g., optical or magnetic device) for characterizing at least one property of the magnetic particles that are attached or attracted to the surface 143. This device could be an integral part of the device 104, or it could be a part of the magnet 150, or it could be a discrete component apart from other components of the apparatus 100. Such a device may be used to detect the presence of the particles, and also to determine parameters related to the particle, for example, the size, quantity, concentration, or density of the particles that are attracted to the surface 143.

One embodiment of the apparatus 100 includes an identification device for allowing an operator or computer to identify the apparatus 100 or a particular component (e.g., cartridge 103 of FIG. 1B) of the system for tracking usage of the system or component. The identification device may include a symbol or image such as a bar code, an identification number, or other identifying mark. The identification device may include an actual component, passive or active, such as an RFID tag, an integrated circuit or other such component known in the art for providing identifying information. Many such devices are known in the art, although any contemplated identification device may be used.

EXAMPLE

PSA in Calibrator

By way of illustration, an experiment was conducted in which data was acquired using the assay measurement apparatus 100 of FIG. 1A, according to principles of the present invention. Dynal tosyl-activated super paramagnetic beads, functionalized with anti-Prostate Specific Antigen (PSA) capture antibody (PN 90205, Scripps Laboratories Inc. with offices in San Diego, Calif.) were exposed to samples. The samples comprised 1×PBS (Phosphate Buffered Saline) and 1% Bovine Serum Albumin (BSA), spiked with approximately 0 pg/mL, 10 pg/mL, 100 pg/mL and 500 pg/mL of free PSA [Fitzgerald Industries International, Inc. with offices in Concord, Mass.]. A bead concentration on the order of approximately $2\times10^4$ beads/mL with respect to sample was used in the experiment. Spiked samples where incubated with beads with gentle continuous agitation for 1 hour.

Eight of the Flexural Plate Wave (FPW) devices 104 of FIG. 2 provided on a single chip in a cartridge (not shown) were functionalized with complimentary anti-PSA antibodies (PN 90197, Scripps Laboratories Inc. with offices in San Diego, Calif.) after being first primed with 1×PBS containing 0.05% Tween 20 (polyethylene glycol sorbitan monolaurate) [Sigma-Aldrich Co. with offices in St. Louis, Mo.]. A baseline measurement (similarly as described previously herein) of eight individual frequencies, each corresponding to tracked sensor phases, each with respect to reference signals, was made at about 17800 seconds. Tracking phases are initially selected for each device to be within a resonance band of the device, near a frequency where the magnitude of response is near a peak value and where the phase response has significant linear range with respect to frequency change. When tracking the sensor phases, at each time point, individual device tracking frequencies are found by 1) sweeping each device over a range of frequencies and recording the phase of response at each excitation frequency with respect to a reference signal, 2) fitting a function relating excitation frequencies to measured phase for each device, and 3) using that function to compute the tracking frequency corresponding to the previously determined tracking phase. In this embodiment, the devices are operated near 20 MHz and the sweep range is approximately 20 kHz. Over this range, the phase characteristic is substantially linear allowing the fit function to be linear. The reference signal for each device comprises the output of a network of passive electrical components, resistors and capacitors, simultaneously driven by the excitation. The reference network is selected to match the attenuation and provide a preferred phase shift for the devices near resonance. Baseline frequencies are referenced to, and normalized by, the tracked frequency and are shown as parts per million (ppm) at a selected point in time.

The sensing surface 143 of each device 104 was functionalized with capture agent. Gold coated chips were cleaned using an oxygen plasma source in which typical processing conditions were about 50 W for about 2 minutes. The chips were subsequently immersed in pure ethanol for 30 minutes. Next, the chips were transferred to a 0.5 mM solution of biotin PEG disulfide solution (Cat No. 41151-0895, Polypure AS with offices in Oslo, Norway) in ethanol and allowed to incubate overnight. The chips were transferred back into a pure ethanol solution for 30 minutes. The chips received a brief, final ethanol rinse and were blown dry using a nitrogen stream. Variations on preparation conditions can be made with similar results achieved. The resultant biotinylated surface of the devices 104 was coated with Neutravidin (PN 31000, Pierce Biotechnology, Inc. with offices in Rockford, Ill.) by flowing a 10 µg/ml solution of neutravidin over the biotinylated surface for 1 hour. Antibody was biotinylated according to the manufacturer's instructions (PN F-6347, Invitrogen Corporation with offices in Carlsbad, Calif.) and then coupled to the neutravidinated surface, by flowing 5 µg/ml solution of the biotinylated antibody (diluted into 1×PBS 0.1% BSA buffer), over the neutravidin coated surface for 1 hour.

Figure 3:
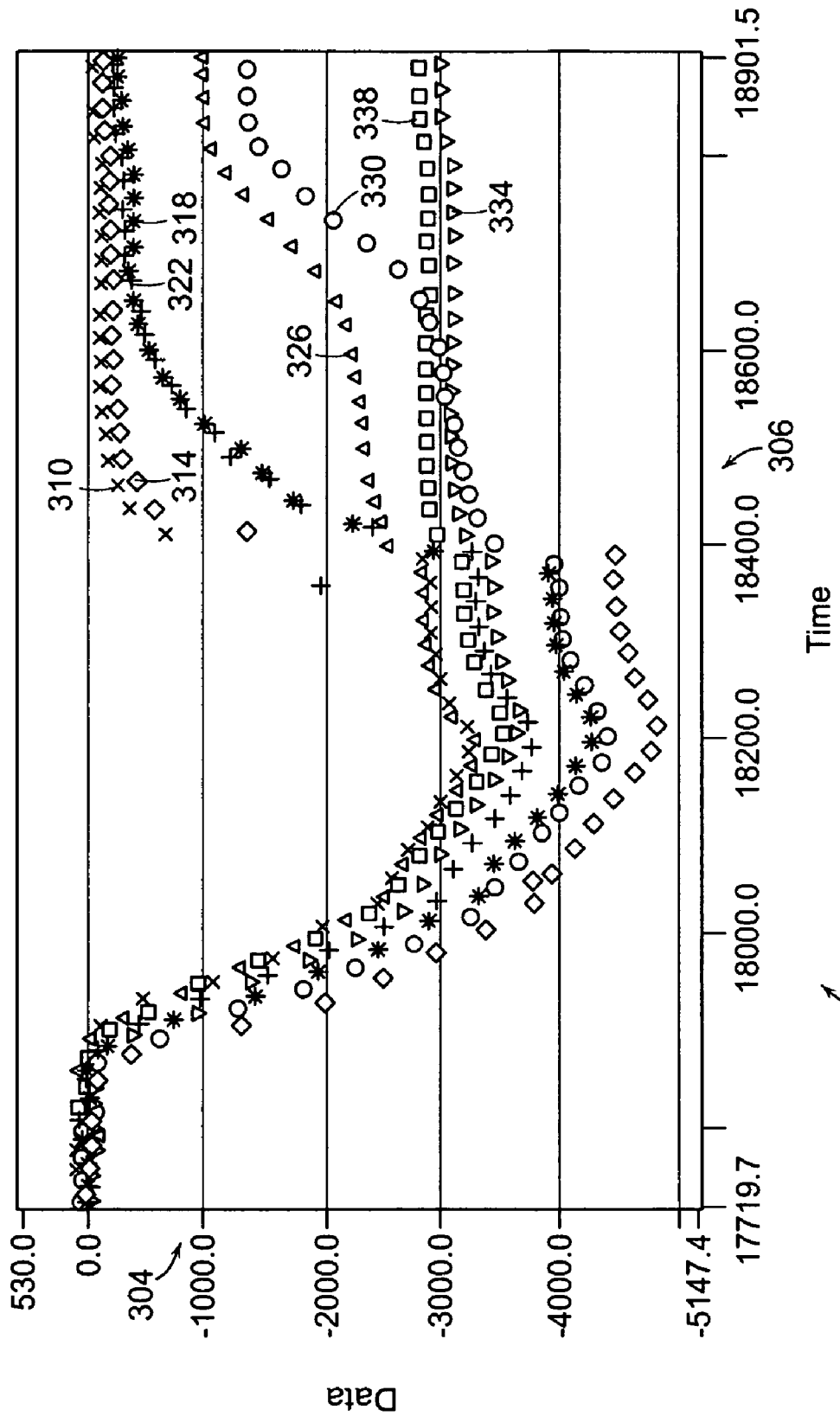
FIG. 3 is a graphical representation of assay measurement data versus time prior to application of methods of the present invention.

FIG. 3 is a graphical illustration of a plot 300 of data acquired versus time, prior to processing the data according to principles of the present invention. The Y-Axis 304 of the plot 300 is the change in tracked frequency (similarly as previously described herein corresponding to the established tracked phases), referenced to and normalized by a tracked frequency at a selected point in time. The X-Axis 306 of the plot 300 is time in units of seconds. Curves 310, 314, 318, 322, 326, 330, 334 and 338 are plots of discrete data points of the experimental results associated with each of the eight devices tested. Curves 310 and 314 are plots for the samples containing approximately 0 pg/ml of free PSA. Curves 318 and 322 are plots for the samples containing approximately 10 pg/ml of free PSA. Curves 326 and 330 are plots for the samples containing approximately 100 pg/ml of free PSA. Curves 334 and 338 are plots for the samples containing approximately 500 pg/ml of free PSA. In some embodiments, data points are omitted that are, for example, outside the normal variation observed in the curves. For example, spurious data points that vary by more than an order of magnitude in value relative to adjacent data points may be omitted from subsequent analysis. The data points may be removed from the data by, for example an operator or by a computer program.

PSA sample was introduced and simultaneously a magnetic field was generated near the sensor surfaces 143 from about 17900 to about 18200 seconds. Samples of approximately 0 pg/mL, 10 pg/mL, 100 pg/mL and 500 pg/mL of free PSA were each provided to two different devices 104 (total of eight devices). The samples were flowed over the sensors at approximately 100 µL/min for a total sample run/volume of 500 µL flowing over the sensors. In this manner, Dynal tosyl-activated super paramagnetic beads coated with free PSA were bound to a substantial surface (surface 143) of the devices 104. Each bead was bound to the surface 143 of the devices 104 by a plurality of bonds. Each plurality of bonds giving rise to the discriminatory force with which each binds to the surface of the device. The characteristic of association and dissociation of an ensemble of beads for each sample determines the concentration of analyte in that sample.

At approximately 18200 seconds the sample was replaced with priming buffer (1×PBS, 0.05% Tween 20 (polyethylene glycol sorbitan monolaurate)). As shown in FIG. 3, a change in each of the signals associated with curves 310, 314, 318, 322, 326, 330, 334 and 338 was observed from 18200 seconds to 18400 seconds and represents the change in bulk fluid properties associated with switching from the sample fluids back to the buffer fluid. At approximately 18400 seconds the magnetic field was disengaged. The flow speed of the buffer fluid (1×PBS containing 0.05% Tween 20) was approximately 50 µL/minute between about 18200 seconds and 18400 seconds (corresponding to a flow speed of approximately 1.5 mm/second at the sensor surface 143).

The flow speed was increased over the next 450 seconds (from about 18400 seconds to about 18850) from approximately 50 μL/min to approximately 300 μL/min in linear increments (the flow speed was increased by about 17 μL/min every 30 seconds for 450 seconds then the flow speed was reduced to approximately 50 μL/min). In this manner, a controlled external influence (i.e., the flow speed in this embodiment) was applied to the beads by increasing the flow speed between about 18400 and about 18850 seconds). The portion of curves 310, 314, 318, 322, 326, 330, 334 and 338 between about 18400 and about 18850 seconds represents a signal that is indicative of the change in the amount of beads (and other non-specific material) bound to the sensor surfaces 143 over that time period.

Figure 4:
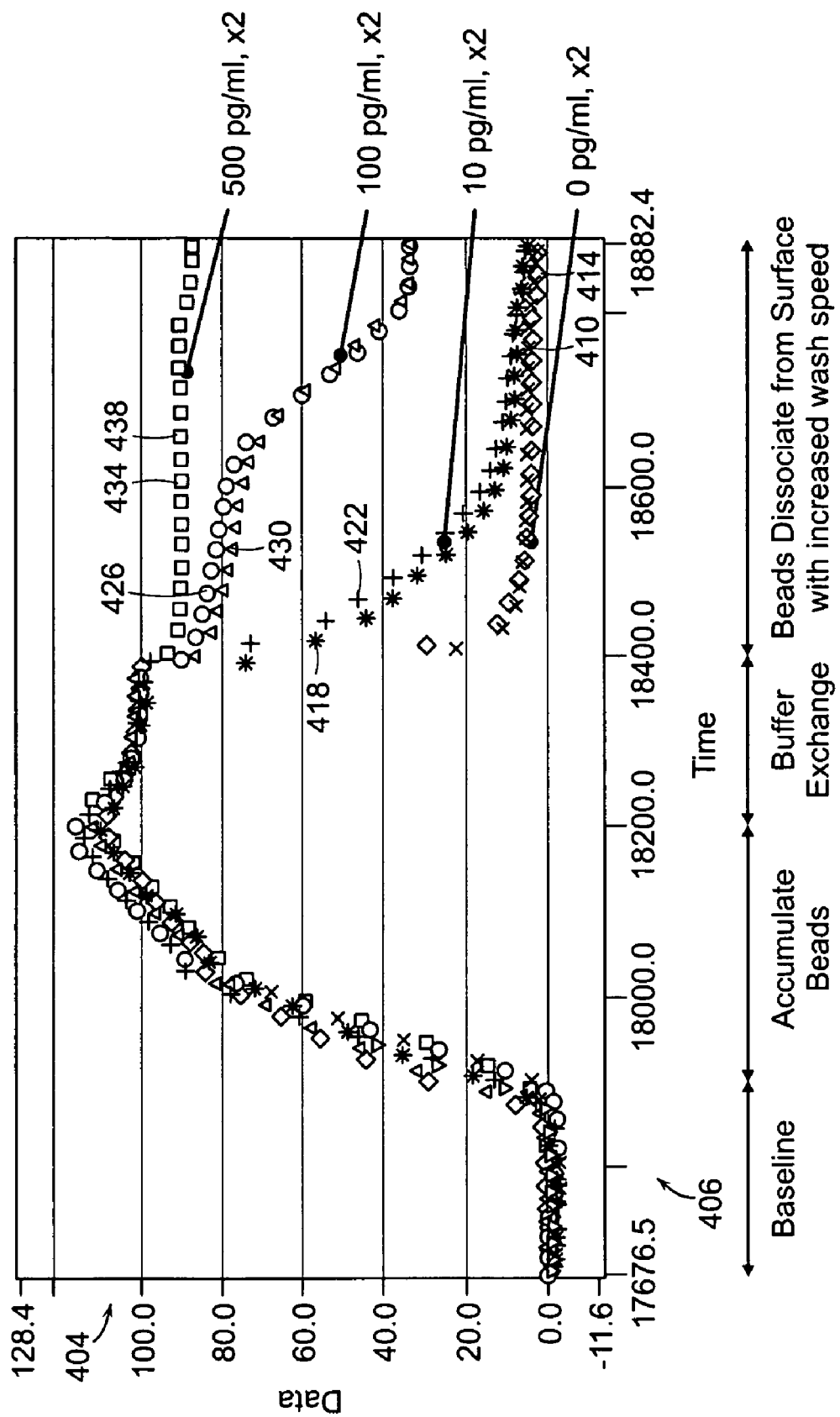
FIG. 4 is a graphical representation of assay measurement date versus time after application of methods of the present invention.

FIG. 4 is a graphical illustration of a plot 400 of the data acquired versus time in FIG. 3, after processing the data according to principles of the present invention. The processed curves 410, 414, 418, 422, 426, 430, 434 and 438 of FIG. 4 correspond to the unprocessed curves 310, 314, 318, 322, 326, 330, 334 and 338 of FIG. 3, respectively. The Y-Axis 404 of the plot 400 is the change in relative magnitude of the signal output by the device 104 (in parts per million) at a tracked sensor phase near the resonance of the device 104. The X-Axis 406 of the plot 400 is time in units of seconds.

The processed curves 410, 414, 418, 422, 426, 430, 434 and 438 were determined by first normalizing the data associated with the unprocessed curves (310, 314, 318, 322, 326, 330, 334 and 338). The data for each curve (310, 314, 318, 322, 326, 330, 334 and 338), shown in parts per million of tracked frequency, was further normalized by the value of that curve at about 18350 seconds and referenced to the baseline frequency that was measured before introduction of the sample fluid. Each data curve was thereby scaled to a value of 100% at about 18350 seconds compared to when sample is introduced. The data associated with each of the normalized curves was then integrated with respect to time over the 450 seconds (from about 18400 seconds to about 18850 seconds) after the magnetic field was removed at about 18400 seconds. The integration was performed by accumulating respective device signal levels, each interval level multiplied by the respective interval time periods, and dividing the final sum by the period over which the sum was performed. This provides the time normalized amount of material elements (beads) bound to the surfaces 143 of the devices, and these values are shown here to be a measure of concentration of analyte associated with each sample. In this manner, the concentration of analyte is determined based on the change in the amount of material elements bound to the surfaces 143 of each device 104 during the period of time between about 18400 seconds to about 18850 seconds. As shown in FIG. 4, approximately 10 pg/mL of free PSA was detected within less than about 9 minutes of introducing the sample into the system.

Alternative normalization and integration methods can be employed in alternative embodiments of the present invention. For example, rather than the output of each device being normalized with respect to the accumulated load on a device by device basis, a group of devices may be normalized by a single device response within the same group on a single chip. In this case the relative rate of material element loading during sample flow, between different devices, factors into the results. An alternate integration method could involve accumulating signal over distinct segmented periods of time, normalizing each by the respective periods of time, and further adding together the weighted sum of these segments. In a further example, the segmented periods of time that have been normalized and integrated can be summed with normalized signals observed at a particular point in time, after a period of controlled external influence. These methods can reduce bias from signal anomalies that can occur with sudden changes in external influences, and spurious environmental effects.

In other embodiments, accurately controlled flow rates (e.g., 1-1000 μL/min), can be applied resulting in lower limits of detection when compared to the background measurements, and larger dynamic range of measurements. In some embodiments, the flow rates are continuously increased, resulting in a continuous change in the external influence on the associated material elements (e.g., microparticles). In some embodiments, the flow rates are increased in a nonlinear fashion (e.g., increases in flow rate that are logarithmically spaced from 1-1000 μL/min), enabling longer periods of integration time at lower flows which improves the signal to background noise ratio and enables larger dynamic range.

Alternative types of assay measurement apparatuses or apparatus components can be used in alternative embodiments of the invention. In some embodiments, the material elements (e.g., beads, microspheres, paramagnetic particles, magnetic particles or gold particles) are bound to a surface of a resonant device. The resonant device can be for example, an acoustic device, flexural plate wave device, surface acoustic wave device, lamb wave device, resonant cantilever device, shear harmonic surface acoustic wave device, acoustic plate mode device or quartz crystal microbalance device.

Various apparatuses are contemplated for use in measuring the signals that are indicative of the change in the amount of material elements bound to the surface. Apparatuses that can be used include, for example, surface plasmon resonance apparatuses, resonant devices, acoustic devices, flexural plate wave devices, quartz microbalance devices, fluorescence measurement apparatuses and microscopes. In some embodiments, the surface to which the material elements are bound is also a surface of the apparatus used to measure the change in the number of bound material elements.

In some embodiments, optical signal measurements are made that are indicative of the change in the amount of material elements bound to the surface relative to the normalized exposure. In such instances, methods of the invention can involve, for example, imaging and counting the material elements, measuring the spatially integrated fluorescence emitted from the material elements, measuring the spatially integrated light scattering from the material elements, measuring the surface Plasmon resonance change from material elements or measuring the attenuation of light reflected from or transmitted through the surface.

A variety of influences can be used as the external influence applied to the material elements, the surface to which the material elements are bound, or to the substances or binding materials disposed between the material elements and the surface. As described previously herein, the external influence can be a fluid flowing through, over or across the material elements that are bound to the surface. In some embodiments, a relative acceleration is provided between the material elements and the surface. In some embodiments, the material elements are magnetic and an opposing magnetic gradient is applied to the material elements with, for example, optional source 150a of FIG. 1A).

In some embodiments, the amplitude of the relative displacement is increased between the material elements and the surface. In some embodiments, the material elements respond to electrophorectic or dielectrophoretic forces generated by a constant or time-varying electric field. In some embodiments, the external influence acts on the binding force strength between the material elements and the surface. This can be accomplished by, for example, changing the pH of a fluid, introducing a denaturant or varying temperature in the proximity of the material elements on the surface. In some embodiments, the material elements are bounds to the surface of a resonant device that generates acoustic fields or flow fields at the surface of the resonant device which act against the binding force between the material elements and the surface.

Variations, modifications, and other implementations of what is described herein will occur to those of ordinary skill in the art without departing from the spirit and the scope of the invention and are considered to be encompassed thereby. Accordingly, the invention is not to be defined only by the preceding illustrative description.

What is claimed is:

1. A method comprising:
   flowing a sample including a plurality of magnetic particles and an analyte through a fluid chamber including a detection surface comprising a resonant acoustic device having a vibrating membrane and a first capture agent linked to the detection surface, wherein the sample includes at least one magnetic particle functionalized with a second capture agent capable of binding the analyte;
   binding, while flowing the sample through the fluid chamber, a first portion of the plurality of the magnetic particles to the detection surface by linking of the second capture agent to the analyte to the first capture agent;
   applying, while flowing the sample through the fluid chamber, a magnetic field to the fluid chamber to associate a second portion of the plurality of magnetic particles with the detection surface, wherein the second portion of the plurality of magnetic particles are not linked to the detection surface by the analyte;
   measuring a first signal corresponding to a total amount of the plurality of the magnetic particles bound to the detection surface or associated with the detection surface during a first period of time to establish a normalized exposure;
   changing an amount of the magnetic field applied to the plurality of the magnetic particles during a second period of time relative to the magnetic field applied during the first period, the change in the amount of the magnetic field sufficient to cause at least a portion of the second portion of the plurality of magnetic particles to dissociate from the detection surface of the resonant acoustic device while the first portion of the plurality of the magnetic particles remain affixed to the detection surface by linking of the second capture agent to the analyte to the first capture agent;
   measuring a second signal during the second period of time; and
   comparing the first signal to the second signal to determine a change in the amount of the plurality of magnetic particles bound to the surface relative to the normalized exposure.

2. The method of claim 1 further comprising utilizing the change in the amount of the plurality of magnetic particles to determine a concentration of the analyte linked to the detection surface.

3. The method of claim 1 wherein the change in the amount of the magnetic field is sufficient to cause at least a portion of the first portion of the plurality of magnetic particles to dissociate from the detection surface of the resonant acoustic device.

4. The method of claim 1 further comprising applying an external influence to the plurality of magnetic particles to cause at least a portion of the second portion of the plurality of magnetic particles to dissociate from the detection surface of the resonant acoustic device while the first portion of the plurality of the magnetic particles remain affixed to the detection surface by linking of the second capture agent to the analyte to the first capture agent.

5. The method of claim 1 further comprising integrating values of the measured signal with respect to time to determine a time-averaged amount of the plurality of magnetic particles bound to or associated with the surface.

6. The method of claim 4 wherein the external influence comprises flow of a fluid over, through or across the plurality of magnetic particles.

7. The method of claim 4 wherein the external influence comprises relative acceleration between the plurality of magnetic particles and the detection surface.

8. The method of claim 4 wherein the external influence comprises a constant or time-varying electric field to which the plurality of magnetic particles are exposed to induce an electrophoretic or dielectrophoretic force that acts on the plurality of magnetic particles.

9. The method of claim 4 wherein the external influence comprises an acoustic field or fluid flow field generated by the resonant acoustic device to which the plurality of magnetic particles are exposed.

10. The method of claim 4 wherein the external influence comprises an alteration of the binding force strength between the plurality of magnetic particles and the surface.

11. The method of claim 10 wherein an alteration of the binding force strength comprises altering pH of a fluid, flowing a denaturant over the plurality of magnetic particles altering temperature of a fluid, or combinations thereof.

12. The method of claim 4 wherein the external influence comprises an amplitude of a relative displacement between the plurality of magnetic particles and the surface being increased.

13. The method of claim 4 further comprising varying the external influence over the second period of time.

14. The method of claim 1 wherein the plurality of magnetic particles are magnetic particles, paramagnetic particles, gold particles, microspheres or beads.

15. The method of claim 1 wherein the plurality of magnetic particles associate with the detection surface of the resonant acoustic device via specific associations, non-specific associations, cross-reactive associations, ionic bonds, covalent bonds, van der Waals bonds, hydrogen bonds or polar bonds.

16. The method of claim 4 wherein the external influence comprises a force on the plurality of magnetic particles that competes with the association between the plurality of magnetic particles and the detection surface.

17. The method of claim 6 wherein the fluid comprises a wash buffer.

* * * * *